United States Patent [19]

Yang

[11] Patent Number: 5,466,768

[45] Date of Patent: * Nov. 14, 1995

[54] ULTRAVIOLET LIGHT ABSORBING COMPOUNDS, SILICONE COMPOSITIONS AND METHODS FOR MAKING SAME

[75] Inventor: Shih-Liang S. Yang, Laguna Hills, Calif.

[73] Assignee: Allergan, Inc., Irvine, Calif.

[*] Notice: The portion of the term of this patent subsequent to Nov. 17, 2009, has been disclaimed.

[21] Appl. No.: 239,175

[22] Filed: May 6, 1994

Related U.S. Application Data

[60] Division of Ser. No. 969,912, Nov. 2, 1992, Pat. No. 5,352,753, which is a continuation-in-part of Ser. No. 691,149, Apr. 25, 1991, Pat. No. 5,164,462, which is a continuation-in-part of Ser. No. 959,394, Oct. 9, 1992, Pat. No. 5,376,737.

[51] Int. Cl.$^6$ ........................................................ C07F 7/10
[52] U.S. Cl. ................................ 528/15; 528/27; 525/479
[58] Field of Search .......................... 528/27, 15; 525/479

[56] References Cited

U.S. PATENT DOCUMENTS

| | | |
|---|---|---|
| 4,250,268 | 2/1981 | Rody et al. . |
| 4,316,033 | 2/1982 | Ching . |
| 4,380,643 | 4/1983 | Yoshida et al. . |
| 4,528,311 | 7/1985 | Beard et al. . |
| 4,555,545 | 11/1985 | Kimura et al. . |
| 4,608,050 | 8/1986 | Wright et al. . |
| 4,612,358 | 9/1986 | Besecke et al. . |
| 4,805,254 | 2/1989 | Dunks et al. . |
| 4,859,759 | 8/1989 | Maycock et al. . |
| 4,868,251 | 9/1989 | Reich et al. . |
| 4,872,877 | 10/1989 | Tiffany . |
| 4,960,898 | 10/1990 | Sakuta et al. . |
| 5,102,707 | 4/1992 | Canivenc et al. . |
| 5,164,462 | 11/1992 | Yang . |

FOREIGN PATENT DOCUMENTS

| | | |
|---|---|---|
| 0282294 | 9/1988 | European Pat. Off. . |
| 0335312A3 | 10/1989 | European Pat. Off. . |
| 0354145 | 2/1990 | European Pat. Off. . |
| 02882119A2 | 9/1990 | European Pat. Off. . |
| 0388218 | 9/1990 | European Pat. Off. . |
| 0434619A2 | 6/1991 | European Pat. Off. . |
| 0488145A2 | 6/1992 | European Pat. Off. . |
| 02051542 | 2/1990 | Japan . |
| 2077747A | 12/1981 | United Kingdom . |
| WO8604342 | 7/1986 | WIPO . |
| WO8804299 | 6/1988 | WIPO . |
| WO9219625 | 11/1992 | WIPO . |

OTHER PUBLICATIONS

Contact Lenses, A Clinical Approach to Fitting, Robert H. Hales, 59,199–204 (1978).
Contact Lens Handbook, James R. Lee, 5, 28–32, 70, 71, 117.

Primary Examiner—George F. Lesmes
Assistant Examiner—Helen F. Lee
Attorney, Agent, or Firm—Frank J. Uxa

[57] ABSTRACT

An ultraviolet light absorbing silicone composition is disclosed which comprises silicone base polymer and ultraviolet light absorbing component present as, or derived from, one or more silicon-containing ultraviolet light absorbing benzotriazole derivatives. Also disclosed are methods for producing such silicone compositions and derivatives. Such silicone compositions, which are preferably optically clear, are useful as lens materials.

17 Claims, No Drawings

ULTRAVIOLET LIGHT ABSORBING COMPOUNDS, SILICONE COMPOSITIONS AND METHODS FOR MAKING SAME

RELATED APPLICATION

This application is a division of application Ser. No. 07/969,912, filed Nov. 2, 1992, now U.S. Pat. No. 5,352,753 which, in turn, is a continuation-in-part of application Ser. No. 07/691,149, filed Apr. 25, 1991, now U.S. Pat. No. 5,164,462, and a continuation-in-part of application Ser. No. 07/959,394 filed Oct. 9, 1992, now U.S. Pat. No. 5,376,737 each of which applications is incorporated in its entirety by reference herein.

BACKGROUND OF THE INVENTION

This invention relates to ultraviolet (UV) light absorbing compounds, polymer compositions and methods for making same. More particularly, the invention relates to UV light absorbing compounds and to polymer compositions including silicone polymers which compositions include, or are partially derived from, such UV light absorbing compounds, and to methods for producing such UV light absorbing compounds and polymer compositions. The subject polymer compositions, which are preferably optically clear, may be used in the fabrication of UV light absorbing ocular devices such as corneal contact lenses, intraocular lenses, and corneal intrastromal implant lenses.

The incident light entering the eye is composed of the entire spectrum of wavelengths including the ultraviolet, visible, and infrared. The cornea preferentially filters UV light in the range of about 300 nm to about 400 nm. Thus, in the eye with its natural lens in place relatively little radiation of wavelengths less that about 400 nm reaches the posterior intraocular structures, e.g., the vitreous humor and the retina.

In the aphakic individual, i.e., that individual who has had the natural crystalline lens removed, there is a loss in protection for the retina from UV light in the above-noted range. Thus, the use of UV light absorbing contact or intraocular lenses is particularly important for the aphakic person. It is further believed that UV light screening spectacles or contact lenses may retard the development of a cataract in the natural lens.

Although low molecular weight, non-polymerizable UV light absorbing compounds of various types are effective in blocking UV radiation when compounded into polymer formulations, their extractability in various media may limit their utility. Also, such UV light absorbing compounds have a potential for phase separation from the polymer formulation. This so-called "blooming" effect is dependent on how soluble the UV light absorbing compound is in the polymer. These problems are remedied by the synthesis of polymerizable, UV light absorbing monomers which can be covalently coupled into the polymer matrix. These covalently bonded UV light absorbing monomers are not extractable and do not phase separate from the remainder of the polymer. Articles fabricated from UV light absorbing silicone compositions incorporating these polymerizable UV light absorbing monomers therefore maintain stable ultraviolet screening characteristics and do not exhibit haze or blooming. The "blooming" problem could be solved by providing a UV light absorbing compound which, even though it is not polymerizable, has increased solubility in the polymer.

Reich, et al U.S. Pat. No. 4,868,251 discloses UV light absorbing compositions comprising silicone elastomers and, covalently bonded thereto, a UV light absorbing component derived from one or more of certain vinyl functional benzotriazole monomers. In preparing the final composition, heat and/or a co-solvent, such as isopropanol, is often needed to dissolve the UV light absorbing monomer in the silicone prepolymer. It would be advantageous to provide a UV light absorbing component which has substantial compatibility or solubility in the solvent. This would simplify, ease and quicken the manufacture of the final UV light absorbing polymeric composition. Further, an UV light absorbing component with enhanced compatibility and/or solubility would result in a monomer/prepolymer mix with a relatively long shelf life so that the mix could be produced and stored well before its ultimate use with little or no phase separation or other detrimental effect.

European Patent Publication No. 0282294 discloses vinylsilylalkoxy arylbenzotriazole monomers which are incorporated into optically clear silicone polymers. These silicon-containing monomers are taught as being more reactable with the silicone polymers than are non-silicon-containing monomers so that a more complete reaction and less non-reacted monomer are obtained. This publication still discloses the need for relatively high temperature, on the order of 90° C., to solubilize the monomer in the silicone prepolymer. Because of these elevated temperatures, the monomer is often mixed with only one portion or part of a conventional two part silicone formulation. The resulting additional mixing step adds to the cost and complexity of the final polymeric composition manufacturing process. Also, the limited solubility of this monomer reduces the effective shelf life of the prepolymer/monomer mixture.

Clearly, it would be advantageous to provide a new, preferably more soluble, class of UV light absorbing compounds, particularly for use in silicone polymers.

SUMMARY OF THE INVENTION

New UV light absorbing compositions and compounds and methods for producing such compositions and compounds have been discovered. The present compounds have excellent UV light absorbing properties and may be used in a variety of materials to provide desired UV light absorbance. These compounds are particularly useful for incorporation in the present compositions. The present compositions comprise silicone elastomer and UV light absorbing component present as, or derived from, one or more of certain UV light absorbing compounds. The present UV light absorbing compounds are readily soluble in the silicone prepolymer or prepolymers often without heating and/or the use of a co-solvent. Additionally, mixtures of the present UV light absorbing compounds and silicone prepolymers remain stable, for example, substantially homogenous, over long periods of time, i.e., have long shelf lives, even at temperatures of less than about 0° C. These features enhance the ease of manufacturing ocular products, such as lenses, from the present compositions. Mixtures of the UV light absorbing compound/silicone prepolymer/cross-linking agent are useful, for example, for producing solid, cured or cross-linked lens structures for the eye. The present compositions can be used to absorb radiation in the wavelength range of about 300 nm to about 400 nm. These compositions are preferably optically clear and can be utilized for the manufacture of corneal contact, intraocular and corneal intrastromal lenses. There is no significant phase separation, and preferably no significant extraction, of the UV light absorbing component, for example, during normal use of the compositions or lenses. The present compounds and compositions can be made by methods which are very effective and relatively easy and straight forward to practice.

In one embodiment, the present UV light absorbing compounds comprise UV light absorbing benzotriazole derivatives having one of the following structures or formulas:

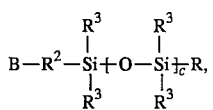 (1)

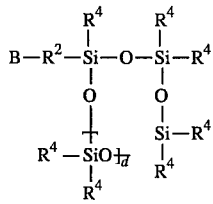 (2)

and mixtures thereof, wherein B is

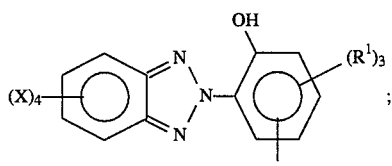

each X is independently selected from the group consisting of H, monovalent hydrocarbon radicals, monovalent substituted hydrocarbon radicals, hydroxyl radicals, amino radicals, carboxyl radicals, alkoxy radicals, substituted alkoxy radicals, and halogen radicals; each $R^1$ is independently selected from the group consisting of H and alkyl radicals, alkoxy radicals, hydroxyl radicals, amino radicals and carboxyl radicals; $R^2$ is selected from divalent hydrocarbon radicals, divalent substituted hydrocarbon radicals, oxo, divalent oxyhydrocarbon radicals and divalent substituted oxyhydrocarbon radicals; each $R^3$ is independently selected from alkyl radicals, substituted alkyl radicals, alkoxy radicals, substituted alkoxy radicals, H, alkenyl radicals, substituted alkenyl radicals, $R^2$-B, aryl radicals, substituted aryl radicals and fluoro radical; R is selected from $R^3$, H, alkenyl radicals and substituted alkenyl radicals, alkenoxy and substituted alkenoxy radicals, and acryloxy alkyl and substituted acryloxy alkyl radicals; each $R^4$ is independently selected from the group consisting of R and $R^3$, provided that at least one of the $R^4$s is R; c is an integer in the range of 1 to about 10,000; and d is an integer in the range of 0 to about 100. In one particularly useful embodiment, where the UV light absorbing compound is polymerizable, R is selected from H, alkenyl radicals and substituted alkenyl radicals, alkenoxy and substituted alkenoxy radicals, and acryloxy alkyl and substituted acryloxy alkyl radicals. If R is other than H, R preferably contains a terminal carbon-carbon double bond.

The UV light absorbing compositions of the present invention are preferably optically clear, stable materials useful in the fabrication of corneal contact lenses, corneal intrastromal lenses and intraocular lenses. About 0.05% or 0.1% to about 5% by weight of the UV light absorbing component is preferably included in the composition to yield the appropriate UV light blocking efficiency, e.g., in samples of thickness comparable to the final lens products. For example, the UV light absorbing compositions of the present invention can be formulated to completely block ultraviolet radiation in the range of about 300 nm to about 390 nm and to display about 2% to about 20% transmittance at 400 nm for 0.75 mm thick samples.

The UV light absorbing silicone polymeric compositions substantially retain the physical characteristics of the non-UV light absorbing silicone polymeric compositions. The silicone compositions are such that the UV light absorbing component may be covalently attached thereto. Suitable silicone elastomers include, for example, two part platinum catalyzed, vinyl/hydride, addition cured polysiloxanes, such as polydimethylsiloxanes, poly dimethyl-diphenyl siloxanes, poly methyl-phenyl siloxanes, and polyorganofluorosiloxanes, as well as other addition cured polyorganosiloxanes and the like and mixtures thereof.

The present polymerizable or functional UV light absorbing compounds or monomers are preferably reacted with hydride or vinyl functional siloxane prepolymers and/or with hydride or vinyl functional cross-linking or cross-linker agents or components to covalently attach the UV light absorbing component. The cross-linking components are preferably components of a two-part platinum catalyzed, addition cured silicone elastomer formulation. The UV light absorbing component is preferably attached to the prepolymer and/or to a siloxane cross-linking component by a platinum catalyzed reaction. For example, the UV light absorbing monomer may act to form a bridging group similar to that which forms when the siloxane cross-linking component reacts with the siloxane prepolymer in the normal curing process to form the silicone elastomer.

DETAILED DESCRIPTION OF THE INVENTION

The present invention relates to an ultraviolet light absorbing composition comprising a silicone elastomer and an effective amount of UV light absorbing component, which may be physically mixed with and/or covalently bonded to (and a part of) the silicone elastomer.

The present UV light absorbing compounds, for example, which are the UV light absorbing components of the present compositions, or from which the UV light absorbing components of the present compositions are derived, comprise one or more UV light absorbing benzotriazole compounds having one of the following structures or formulas:

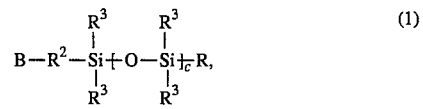 (1)

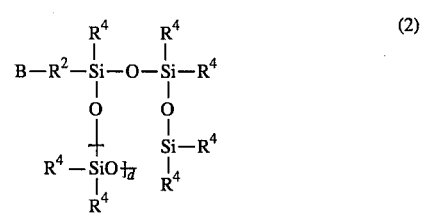 (2)

and mixtures thereof, wherein B is

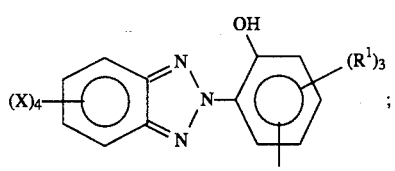

each X is independently selected from the group consisting of H, monovalent hydrocarbon radicals and monovalent substituted hydrocarbon radicals, preferably containing 1 to about 8 carbon atoms, hydroxyl radicals, amino radicals, carboxyl radicals, alkoxy radicals and substituted alkoxy radicals, preferably containing 1 to about 6 carbon atoms, and halogen radicals; each $R^1$ is independently selected from the group consisting of H and alkyl radicals, substituted alkyl radicals, alkoxy radicals and substituted alkoxy radicals, preferably containing 1 to about 8, more preferably 1 to about 4 carbon atoms, hydroxyl radicals, amino radicals and carboxyl radicals; $R^2$ is selected from divalent hydrocarbon radicals such as alkylene radicals, divalent substituted hydrocarbon radicals, oxo, divalent oxyhydrocarbon radicals and divalent substituted oxyhydrocarbon radicals, preferably containing up to about 6 carbon atoms and more preferably containing 1 to about 4 carbon atoms, and still more preferably being an alkylene radical containing 1 to about 4 carbon atoms; each $R^3$ is independently selected from alkyl radicals, substituted alkyl radicals, alkoxy radicals, substituted alkoxy radicals, H, alkenyl radicals, substituted alkenyl radicals, $R^2$-B, aryl radicals, substituted aryl radicals, and fluoro radical, preferably from alkyl radicals, alkoxy radicals, aryl radicals and $R^2$-B and more preferably from alkyl radicals, aryl radicals and $R^2$-B; R is selected from $R^3$, H, alkenyl radicals and substituted alkenyl radicals, preferably having 2 to about 6 carbon atoms and more preferably $CH=CH_2$, alkenoxy and substituted alkenoxy radicals, and acryloxy alkyl and substituted acryloxy alkyl radicals; each $R^4$ is independently selected from the group consisting of R and $R^3$, provided that at least one of the $R^4$s is R; c is an integer in the range of 1 to about 10,000, preferably 1 to about 10 and more preferably 1 to about 4; and d is an integer in the range of 0 to about 100, preferably 0 to about 10 and more preferably 0 to about 3. One or more of the $R^3$s may be organo fluoro radicals, for example, fluoro hydrocarbon radicals. In the event the UV light absorbing compound is polymerizable, R is selected from H, alkenyl radicals and substituted alkenyl radicals, alkenoxy and substituted alkenoxy radicals, and acryloxy alkyl and substituted acryloxy alkyl radicals. If R is other than H, R preferably contains a terminal carbon-carbon double bond.

Preferably, at least one of the Xs and $R^1$s is other than H. Particularly useful alkenyl and substituted alkenyl groups from which R is chosen are those which include a terminal carbon-carbon double bond. In one embodiment, the substituent ortho of the phenolic hydroxyl group is other than H.

In the event that any $R^3$ is aliphatic, it preferably contains 1 to about 8, more preferably 1 to about 4, carbon atoms. If any $R^3$ is aromatic, it preferably contains 6 to about 10, and more preferably 6, carbon atoms. In a particularly useful embodiment, each $R^3$ is independently selected from methyl radicals, substituted methyl radicals, phenyl radicals and substituted phenyl radicals, preferably methyl radicals. In the event that an $R^1$ is alkyl, it is preferably tertiary alkyl, and more preferably t-butyl.

Examples of useful monovalent hydrocarbon radicals include alkyl radicals, alkenyl radicals, aryl radicals and the like. Examples of useful alkoxy radicals include methoxy, ethoxy, propoxy, butoxy, hexoxy and the like. A particularly useful halogen group for use as X is chloro. Examples of useful alkyl groups include methyl, ethyl, propyl, butyl, hexyl, octyl and the like. Examples of useful alkenyl radicals include ethenyl (vinyl), propenyl, butenyl, pentenyl, hexenyl, octenyl and the like. Examples of useful alkylene groups include ethylene, propylene, butylene and the like. Examples of useful aryl radicals include phenyl, methyl phenyl, ethyl phenyl, dimethyl phenyl and the like. Examples of useful alkenoxy radicals include ethenoxy, propenoxy, butenoxy, hexenoxy and the like. Examples of useful acryloxy alkyl radicals include acryloxy ethyl, acryloxy propyl, acryloxy butyl, acryloxy pentyl and the like.

The substituted groups referred to herein are exemplified by the above-noted groups (and the other groups referred to herein) substituted with one or more substituent groups including elements such as oxygen, nitrogen, carbon, hydrogen, halogen, sulfur, phosphorus and the like and mixtures or combinations thereof. Examples of useful amine groups include -$NH_2$ and groups in which one or both of the Hs is replaced by a group selected from monovalent hydrocarbon radicals, monovalent substituted hydrocarbon radicals and the like.

In one embodiment, the ultraviolet light absorbing compounds are selected from the group consisting of compounds having the structure (1), noted above, and mixtures thereof. The $R^2$ group is preferably bonded to the ortho position or the para position relative to the phenolic hydroxyl group of B. In the event $R^2$ is bonded to the ortho position relative to the phenolic hydroxyl group of B, it is preferred that all of the $R^1$s are H.

With further regard to B, it is preferred that no more than one of the Xs is other than H, and no more than one of the $R^1$s is other than H. That is, it is preferred that all or all but one of the Xs be H, and all or all but one of the $R^1$s be H. Such "minimally" substituted benzotriazole moieties are relatively easy to produce and provide outstanding ultraviolet light absorbing properties.

A particularly useful class of UV light absorbing compounds is selected from compounds having the following formula or structure

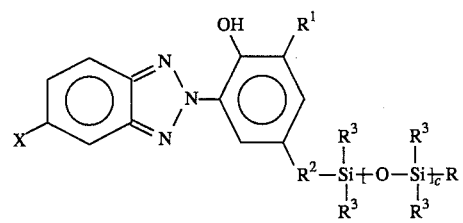

All tautomers, isomers and the like and mixtures thereof of the present UV light absorbing compounds are included within the scope of the present invention. For example, if $R^2$ is an ethylene radical, it may be bonded to the aromatic ring at either the alpha carbon atom or the beta carbon atom. Also, a mixture of such alpha and beta isomers may be used and is included in the scope of the present invention.

The present hydride functional UV light absorbing compounds can be prepared from functional benzotriazole derivatives which include a functional group suitable for reacting with a hydride group of a siloxane to covalently bond the siloxane moiety to the benzotriazole moiety. Examples of useful functional groups which can be included in the functional benzotriazole derivative include hydroxyl radicals (for example, hydroxyl-containing monovalent hydrocarbon radicals), alkenyl groups, substituted alkenyl groups and the like. A number of these functional benzotriazole derivatives are well known and/or are commercially available. Specific examples of useful functional benzotriazole derivatives are the vinyl functional benzotriazole derivatives disclosed in Reich et al U.S. Pat. No. 4,868,251 as starting materials.

The functional benzotriazole derivative is contacted with a siloxane having at least two functional hydride groups if the UV light absorbing compound is to be polymerizable or with a siloxane having only one functional hydride group if a non-polymerizable UV light absorbing compound is to be produced.

Many of the cyclic hydride-containing siloxane components useful to produce the ultraviolet light absorbing compounds of structure (2), noted above, are well known. In a particularly useful embodiment, each of the silicon atoms of such cyclic component has at least one, and more preferably only one, hydride group directly bonded thereto. A number of useful cyclic hydride-containing siloxane component are commercially available. One especially useful such component is tetrahydrotetra-methylcyclotetrasiloxane.

The benzotriazole/siloxane contacting preferably occurs in the liquid phase, using a conventional solvent such as toluene, in the presence of a catalyst, such as a platinum group metal-containing catalyst, for example, a platinum-containing catalyst. Contacting conditions are sufficient to allow the functional group of the functional benzotriazole derivative to react with one of the hydride groups (or the only functional hydride group) of the siloxane. Such conditions can include a temperature in the range of about –600° C. to about 50° C. and reaction times in the range of about 1 hour or less to about 60 hours or more. The resulting hydride functional UV light absorbing monomer or monomers or non-polymerizable UV light absorbing compound or compounds can be recovered, separated and/or purified using conventional techniques, such as distillation, extraction, recrystallization and the like.

The present hydride functional UV light absorbing monomers can be used to prepare the present unsaturation, for example, vinyl, functional UV light absorbing monomers. Thus, such hydride functional monomers can be contacted with a functional component selected from the group consisting of compounds containing a plurality of carbon-carbon multiple bonds, such as butadiene, other dienes and the like, compounds containing a carbon-carbon triple bond, such as acetylene, other acetylene-type compounds and the like, compounds with both a hydroxyl group and a carbon-carbon multiple bond, compounds with an acryloxy alkyl group and a carbon-carbon multiple bond and mixtures thereof. Preferably, the functional component includes at least one terminal carbon-carbon multiple bond. This contacting occurs at conditions effective to chemically react the hydride group of the hydride functional benzotriazole derivative with a functional group present in the functional component, thereby forming the present unsaturation functional monomers which include an R which contains a functional carbon-carbon double bond, preferably with a terminal carbon-carbon double bond.

This contacting preferably occurs in the liquid phase, using a conventional solvent such as toluene, in the presence of a catalyst, such as a platinum group metal-containing catalyst. Contacting conditions are sufficient to allow the hydride group of the hydride functional monomer to react with the functional component. Such conditions can include a temperature in the range of about –60° C. or less to about 50° C. or more and contacting times in the range of about 0.2 hours or less to about 10 hours or more. The resulting unsaturation functional UV light absorbing monomer or monomers can be recovered, separated and/or purified using conventional techniques, such as distillation, extraction, recrystallization and the like.

The platinum group metal-containing catalysts or catalyst components useful in the present invention can be selected from any of the compatible platinum group metal-containing catalysts known to catalyze (or promote) the addition of silicon-bonded hydrogen atoms (hydride groups) to silicon-bonded vinyl radicals. Such catalyst components can be any of the known compatible forms, for example, platinic chloride, salts of platinum, chloroplatinic acid and various complexes. A number of such platinum group metal-containing catalysts are commercially available. The catalyst component is present in an amount effective to promote the desired reaction. For example, such amount may be sufficient to provide at least about 0.1 ppm by weight (and often no more than about 100 ppm by weight) of platinum group metal (calculated as elemental metal) based on the combined weights of the reactant components. In one useful embodiment, the catalyst is chloroplatinic acid complexed with a siloxane such as tetramethylvinylcyclosiloxane (i.e., 1,3,5, 7-tetramethyl-1,3,5,7-tetravinyl-cyclosiloxane).

In accordance with one aspect of this invention, new compositions of matter comprising one or more UV light absorbing silicone elastomers, for example, UV light absorbing polysiloxanes, preferably polyorganosiloxane elastomers, are provided. These compositions are prepared by the incorporation of certain UV light absorbing compounds, for example, by the covalent attachment of certain polymerizable UV light absorbing monomers, as described herein, to silicone materials, preferably to hydride or vinyl functional siloxane base polymers (or pre-polymers) and cross-linking agents or components.

The present compositions preferably further comprise at least one reinforcing agent, such as reinforcing silicone resins, silica and the like which are conventionally used to strengthen silicone elastomeric compositions. The reinforcing agent or agents are present, if at all, in an amount effective to enhance the strength of the composition relative to a substantially identical composition without such agent or agents. For example, the reinforcing agent or agents may be present in an amount up to about 50% by weight or more based on the silicone elastomer present in the composition.

In one embodiment, the base polymers utilized in the present invention have the following structure or formulation:

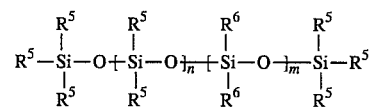

and mixtures thereof, wherein each $R^5$ and $R^6$ is independently selected from the group consisting of H, alkyl radicals, substituted alkyl radicals, alkoxy radicals, substituted alkoxy radicals, alkenyl radicals with a terminal double bond, substituted alkenyl radicals with a terminal double bond, aryl radicals, substituted aryl radicals and fluoro radical, provided that at least one, and preferably at least two, of the $R^5$s is selected from H and olefinically unsaturated groups; and n and m each is an integer independently selected from integers in the range of 0 to about 20,000. In the event that one or more $R^5$s and/or $R^6$s are fluoro radicals, one or more other $R^5$s and/or $R^6$s are preferably organic radicals. One or more of the $R^5$s and/or $R^6$s may be organo fluoro radicals, for example, fluoro hydrocarbon radicals. In one embodiment, each of the $R^5$s, other than those which are selected from H and olifinically unsaturated groups, and the $R^6$s is methyl. Each of the $R^5$s and $R^6$s may be independently selected from alkyl radicals containing 1 to about 4 carbon atoms, fluoro alkyl radicals containing 1 to about 3 carbon atoms, phenyl radicals, substituted aryl radicals, alkenyl radicals containing 2 to about 4 carbon atoms and having a terminal double bond and mixtures thereof.

The cross-linking or cross-linker agents useful in the present invention are preferably components of a two part, silicone elastomer formulation, more preferably a two part, platinum catalyzed vinyl/hydride, addition cured silicone elastomer formulation. In one embodiment, the attachment of the UV light absorbing monomer to the silicone elastomer preferably proceeds by a platinum catalyzed reaction to form an ethylenic bridging group similar to that which forms when a cross-linking molecule binds together siloxane base polymer molecules in the normal curing or cross-linking reaction of the silicone elastomer. Thus, when the base polymer is vinyl functional, the UV light absorbing monomer can be either unsaturation functional or hydride functional, preferably unsaturation functional and more preferably vinyl functional, and the cross-linking agent is hydride functional. Conversely, when the base polymer is hydride functional, the UV light absorbing monomer can be either unsaturation functional or hydride functional, preferably hydride functional, and the cross-linking agent is vinyl functional. In addition, one or more of the base polymer and the cross-linking agent can be both vinyl and hydride functional.

In any event, the silicone elastomer is cross-linked and optically clear, and includes an effective UV light absorbing amount of the UV light absorbing component of the present invention physically mixed and/or covalently bonded within the silicone elastomer. These optically clear, UV light absorbing elastomeric compositions are very effective for inclusion in corneal contact lenses, intraocular lenses and corneal intrastromal lenses. Conventional lens forming techniques, for example, molding techniques, can be used to provide lenses comprising the present UV light absorbing elastomeric compositions.

The preferred siloxane cross-linking agents include a plurality, in particular at least three (3) of functional groups per molecule. Thus, each cross-linking molecule preferably can participate both in the covalent attachment of the UV absorbing monomer as well as in the formation of cross-links between siloxane base polymer molecules.

Suitable cross-linking agents include agents which are conventionally used to produce cross-linked silicone polymers, in particular, polysiloxane elastomers, for example, employing two part platinum catalyzed silicone systems to produce silicone elastomers by vinyl/hydride addition curing. Thus, suitable cross-linking agents are available as a component of many such conventional two part systems. Specific examples of effective cross-linking agents include 1,3,5,7-tetramethylcyclotetrasiloxane (i.e., 1,3,5,7-tetramethyl-1,3,5,7-tetrahydrocyclosiloxane), methylhydropolysiloxane, 1,3,5-trivinyl-1,1,3,5,5-pentamethyl-trisiloxane, methyl vinyl polysiloxane and the like.

The relative amounts of base polymer, UV light absorbing compound and cross-linking agent employed to produce the final composition, e.g., the siloxane elastomer composition, are chosen to provide a final composition having the desired properties, including the desired degree of cross-linking and the desired degree of UV light absorbing ability. The relative amounts of the components utilized varies depending on many factors, for example, on the specific components being employed, and on the application for which the final composition is to be employed. As noted above, conventional two part silicone polymer formulations can be employed. Any adjustments to these conventional formulations (in terms of relative amounts of components) are relatively minor (if required at all) to insure that the relatively minor amount of UV absorbing monomer is effectively incorporated, e.g., physically mixed and/or covalently attached, within the final composition.

The incorporation of the UV light absorbing compound can be made to occur at one or more of various steps in the process of producing an UV light absorbing silicone elastomer. One method is to simply dissolve the UV light absorbing compound into a mixture of the silicone components and to allow the incorporation of the UV light absorbing monomer to occur simultaneous to the formation of the base polymer cross-links. The UV light absorbing compound can be combined with the silicone components just prior to the polymerization reaction, for example, at the mixing or injection head. Also, if desired, the UV absorbing compound can be combined with all or a portion of the silicone components to be polymerized to form a homogeneous mixture which is stored, for example, for relatively long periods of time, on the order of days or weeks, preferably at reduced temperatures, for example about $-80°$ C. to about $0°$ C., before the polymerization reaction. The present benzotriazole-type UV light absorbing compounds have sufficient solubility so that 1% by weight of a benzotriazole-type UV light absorbing compound in accordance with the present invention remains in solution in a curable liquid mixture including all the precursor components of a platinum-catalyzed, cross-linked silicone elastomer even after such mixture is maintained for one week at $-60°$ C. This unique solubility feature allows silicone compositions to be prepared and stored well in advance of the final polymerization/curing without phase separation or precipitation of the UV light absorbing compound, and without uneven or premature curing of the mixture. Alternatively, the present polymerizable UV light absorbing monomer can be pre-reacted with the cross-linking agent to form essentially an UV light absorbing, cross-linking adduct. The composite molecule is subsequently formulated with siloxane base polymer, and preferably additional platinum catalyst, to be cured into the UV light absorbing silicone elastomer. In another embodiment, the present polymerizable UV light absorbing monomer can be introduced into an already formed (cured) silicone elastomer containing reactable groups, such as an elastomer derived from a two part platinum-catalyzed hydride/vinyl siloxane monomer mixture. The polymerizable UV light absorbing monomer is subjected to conditions effective to chemically react the reactable UV light absorbing monomer with the reactable groups of the already formed silicone elastomer. Such subjecting is effective to form a polymer material to which is covalently bonded an UV light absorbing component derived from the polymerizable UV light absorbing monomer. In any case a degree of incorporation of the UV light absorbing compound of greater that 95% is preferably obtained.

The UV light absorbing component covalently attached within the silicone elastomer does not leach out in aqueous or organic solvents, for example isopropanol.

The present UV light absorbing compound often absorbs ultraviolet light strongly in the range of about 300 nm to about 400 nm, and exhibits reduced absorption at wavelengths higher that about 400 nm.

Preferably, the maximum amount of the UV light absorbing compound incorporated in the UV light absorbing composition of the present invention is about 5% by weight. More preferably, the UV light absorbing compound is incorporated into the UV light absorbing composition in an amount in the range of about 0.05% to about 5% by weight and still more preferably about 1% or less by weight, especially about 0.1% to about 1% by weight, based on the total composition. Of course, it is understood that the present polymerizable UV absorbing monomer is not present as such in the composition, but is part of the polymer. However, for convenience and simplicity, in certain instances herein the UV light absorbing monomer is referred to as being present in the polymer. The percentage of UV light absorbing monomer in the polymer referred to herein means the weight percent of such monomer based on the total material included in the composition. The amount of UV light absorbing compound included is that required to give the degree of light absorption desired and is dependent, for example, on the specific UV light absorbing compound or compounds employed, the specific silicone elastomer producing monomer or monomers employed and on the thickness, e.g., the optical path, of the product, e.g., lens, to be made from the polymeric composition. By Beers Law of Absorption, the required amount of absorber is inversely proportional to the optical path length through the lens device. It is often desired that the ultraviolet light transmission at 400 nm be less than about 10 to 15% of the incident light and at 390 nm be less than about 3%. The visible light transmission in the 410–450 nm range often should not be reduced below about 50% of the total light.

As noted above, the present UV light absorbing compounds have substantial compatibility with, e.g., solubility in, the base polymers or prepolymers and/or other silicone, in particular siloxane, molecules (e.g., cross-linking agents) used in producing the final silicone elastomer. Thus, in many instances the UV light absorbing compounds can be dissolved in the prepolymer/compound mix without using a co-solvent and/or without the application of heat. In one embodiment, the present invention involves benzotriazole derivatives effective to absorb, preferably preferentially absorb, UV light and having melting points less than 25° C. Since a uniform mixture can often be prepared at room temperature, that is on the order of about 20° C. to about 25° C., such mixture can be very conveniently prepared, e.g., at room temperature, without concern for premature and uneven curing, since curing often occurs at relatively elevated temperatures.

The present UV light absorbing compounds can be used very effectively as a component of a curable liquid composition comprising, in addition to the UV light absorbing compound, a cross-linkable siloxane base polymer or prepolymer, a cross-linking agent, e.g., as described herein, and a cross-linking catalyst, such as a platinum-containing catalyst as described herein. Such curable liquid composition can be stored at reduced temperature, for example, about −80° C. to about 0° C. for long, on the order of days or weeks, or even indefinite periods of time without concern for precipitation or phase separation of the UV light absorbing compound, or for uneven or premature curing. The curable liquid composition can be injected into the lens capsule of the eye where it is cured at body temperature to a solid, transparent lens which has effective UV light absorbing properties. The use of curable liquid compositions to produce lens structures is disclosed in Wright et al U.S. Pat. No. 4,608,050, which is incorporated in its entirety herein by reference.

The invention will be further described in connection with the following examples which are set forth for purposes of illustration only.

The starting material in Example 1 is 2-(2'-hydroxy-3'-t-butyl-5'-vinylphenyl)-5-chloro-2H-benzotriazole, hereinafter identified as "I", which itself can be produced as described in Reich et al U.S. Pat. No. 4,868,251, which is incorporated in its entirety herein by reference.

EXAMPLE 1

Preparation of 2-[3'-t-butyl-2'-hydroxy-5'-(2"-(7"'-hydro octamethyl tetrasiloxane)ethyl) phenyl]-5-chloro-2H-benzotriazole and 2-[3'-t-butyl-2'-hydroxy-5'-(1"-7"'-hydro octamethyltetrasiloxane)ethyl)phenyl]-5-chloro-2H-benzotriazole mixture The above-noted mixture of the present UV light absorbing monomers is prepared to be used in preparing the mixture of UV light absorbing monomers in Example 2 and the UV light absorbing silicone composition of Example 4.

A 100 ml 3 neck flask equipped with a magnetic stirring bar, an inert gas inlet topped reflux condenser and a thermocouple was charged with 20 g (0.071 mole) 1,1,3,3,5,5,7,7-octamethyltetrasiloxane (from Petrarch Systems, Inc.), 4.0 g (0.012 mole) of I and 10 g dry toluene. The mixture was stirred at room temperature for 1 hour until all of the I dissolved. 1 ml platinum complex solution (Petrarch Systems, Inc., catalog no. PC075) was added and the reaction mixture was stirred at room temperature for 48 hours. Unreacted octamethyltetrasiloxane and toluene were removed by vacuum. 7.5 g (100%) yellow viscous oil, hereinafter identified as "II" was isolated. Using conventional chromatography techniques, II can be further purified, if desired. However, this yellow viscous oil, without further purification, is effective as a polymerizable UV light absorbing monomer mixture. This mixture remained as a liquid even at −60° C.

Mass spectroscopy analysis indicated a molecular weight for II of 610. High pressure liquid chromatography analysis showed essentially two components corresponding to the IIa (80%) and IIb (20%) isomers, shown below. The structures of IIa and IIb isomers and the corresponding concentration ratio were confirmed by UV/VIS, IR, and $^1$H-NMR analyses.

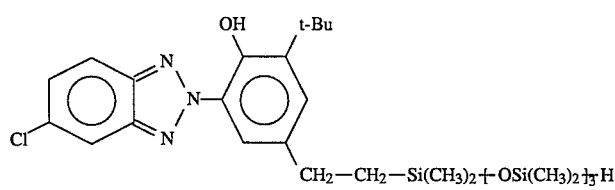

-continued

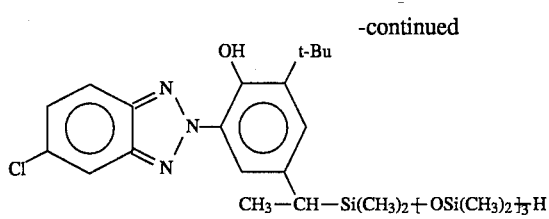

IIb

This mixture is found to have very effective UV light absorbing properties.

EXAMPLE 2

Preparation of a 2-[3'-t-butyl-2'-hydroxy-5'-(2"-(7'"-vinyl octamethyl tetrasiloxane) ethyl) phenyl]-5-chloro- 2H-benzotriazole and 2-[3'-t-butyl-2'-hydroxy-5'- (1"-( 7'"-vinyl octamethyl tetrasiloxane) ethyl) phenyl] 5-chloro- 2H-benzotriazole mixture The above-noted mixture of the present UV light absorbing monomers is prepared to be used in preparing the UV light absorbing silicone composition of Example 3.

A 100 ml, 3 neck flask equipped with a magnetic stirring bar, a reflux condenser, an acetylene gas inlet, and a thermocouple was charged with 2 g of II (the mixture of isomers) and 60 ml dry toluene. The mixture was stirred at room temperature for 10 minutes until all II dissolved. The solution was purged with dry, scrubbed acetylene gas for 2 hours. 1 ml platinum complex solution was added. The reaction mixture was stirred and purged with acetylene continuously at room temperature for 6 hours. Unreacted acetylene and toluene were removed by vacuum. 2.0 g (100%) yellow viscous oil, hereinafter identified as "III", was isolated. Using conventional chromatography techniques, III can be further purified, if desired. However, this isolated product is effective as a polymerizable UV light absorbing monomer mixture. This mixture remained as a liquid even at −60° C.

Mass spectrometry analysis indicated a molecular weight for III of 636. High pressure liquid chromatography analysis showed two components corresponding to the IIIa (80%) and IIIb (20%) isomers, shown below. The structures of the IIIa and IIIb isomers and the corresponding concentration ratio were confirmed by UV/VIS, IR, and $^1$H-NMR analyses.

EXAMPLE 3

Preparation of UV Absorbing Silicone

A glass beaker was charged with 10.20 g of part A, and 10.10 g of part B of a fast cure silicone RTV (McGhan Nusil Corporation Med-6230), and 0.066 g of III (the mixture of isomers). The contents were mixed thoroughly with a glass rod at room temperature. The resulting mixture was deaerated under vacuum and cured at 100° C. for 15 minutes in a mold into a 0.78 mm thick film. This film was extracted with toluene for 8 hours. Both the original film (pre-extraction), which included about 0.32% by weight of the UV light absorbing component, and the extracted film (post extraction) were optically clear and were tested for UV light absorbance.

Results of these tests are as follows:

| % transmission UV light cutoff (nm) | 0.5% | 1.0% | 10% | 30% | 50% | 70% | 80% |
| --- | --- | --- | --- | --- | --- | --- | --- |
| pre-extraction | 386 | 388 | 396 | 401 | 405 | 410 | 415 |
| post-extraction | 382 | 384 | 393 | 399 | 404 | 409 | 415 |

These results indicate that both the original film and the extracted film have very good UV light absorbing properties. Further, the extracted film showed no significant change in UV light absorbing properties relative to the film before extraction. The minor differences in the transmission profiles of the original and purified films may result from the use of an unpurified form of the UV light absorbing monomer and/or the presence of non-reacted, extractable silicones which are bonded to some of the UV light absorbing monomer and are lost during extraction.

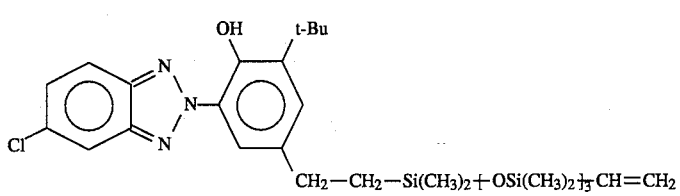

IIIa

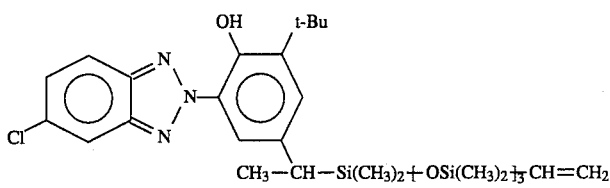

IIIb

This mixture is found to have very effective UV light absorbing properties.

EXAMPLE 4

Example 3 was repeated using a somewhat larger amount of II (the mixture of isomers) in place of III. Both the film before extraction, which included 0.54% by weight of the UV light absorbing component and the extracted film were optically clear and were tested for UV light absorbance. Results of these tests were as follows:

| % transmission UV light cutoff (nm) | 0.5% | 1.0% | 10% | 30% | 50% | 70% | 80% |
|---|---|---|---|---|---|---|---|
| pre-extraction | 391 | 394 | 400 | 405 | 410 | 415 | 419 |
| post-extraction | 389 | 390 | 398 | 403 | 407 | 412 | 417 |

These results indicate that both the original film and the extracted film have very good UV light absorbing properties. Further, the extracted film showed no significant change in UV light absorbing properties relative to the film before extraction.

EXAMPLE 5

Preparation of 2-[3'-t-butyl-2'-hydroxy-5'(2"-heptamethyl trisiloxane ethyl) phenyl]-5-chloro-2H-benzotriazole and 2-[3'-t-butyl-2'-hydroxy-5'-(1"-heptamethyltrisiloxane ethyl) phenyl]-5-chloro-2H-benzotriazole mixture A 100 ml 3 neck flask equipped with a magnetic stirring bar, an inert gas inlet topped reflux condenser and a thermocouple is charged with 20 g (0.09 mole ) 1,1,1,3,3,5,5-heptamethyltrisiloxane (Petrarch Systems, Inc.), 4.0 g (0.012 mole) of I and 10 g dry toluene. The mixture is stirred at room temperature for 1 hr until all I dissolved. 1 ml platinum complex solution (Petrarch Systems, Inc., catalog no. PC-075) is added and the reaction mixture is stirred at room temperature for 48 hrs. Unreacted heptamethyltrisiloxane and toluene are removed by vacuum. A yellow viscous oil, hereinafter identified as IV, is isolated using conventional chromatography techniques, IV can be further purified, if desired. However, this yellow viscous oil, without further purification is effective as a UV light absorbing component. This oil remains a liquid even at −30° C.

Mass spectroscopy analysis indicates a molecular weight for IV of about 550. HPLC analysis shows essentially two components corresponding to the IVa and IVb isomers.

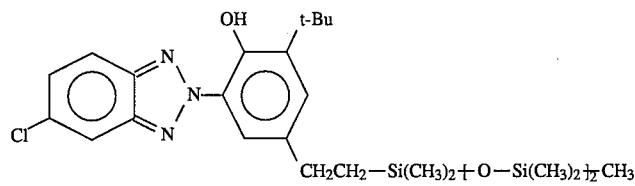

IVa

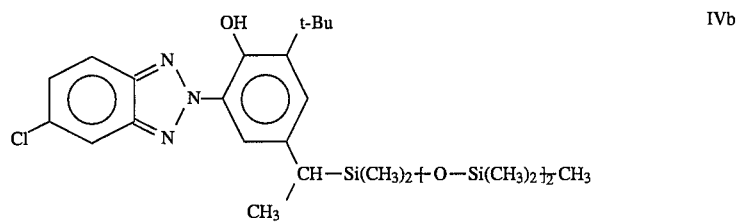

IVb

This mixture is found to have very effective UV light absorbing properties.

EXAMPLE 6

Example 3 is repeated using IV (the mixture of isomers) in place of III. The film is extracted with water, instead of toluene, for 8 hours. Both the film before extraction and the extracted film are optically clear and are tested for UV light absorbance and are found to have very good UV light absorbing properties.

EXAMPLE 7

Example 1 is repeated except that I is replaced by:

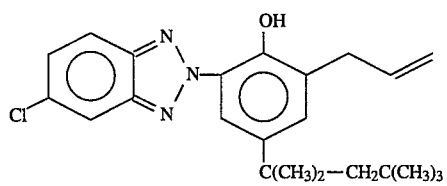

VII

After the reaction is completed, the unreacted octamethyltetrasiloxane and toluene are removed by vacuum to obtain the following compounds:

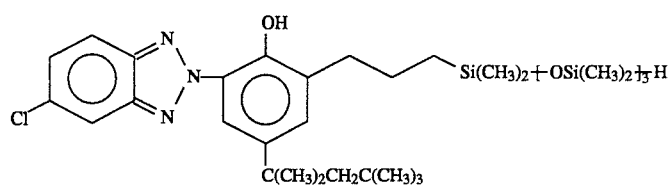

VIIa

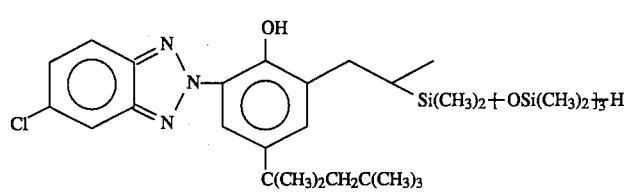

VIIb

This material is a yellow transparent liquid. High pressure liquid chromatography analysis shows two compounds corresponding to VIIa (about 70%) and VIIB (about 30%) isomers.

EXAMPLE 8

Example 2 is repeated except that II is replaced by the VIIa/VIIb mixture obtained in Example 7. A yellow, transparent viscous liquid is obtained. Conventional high pressure liquid chromatography analysis shows the following isomers to be present.

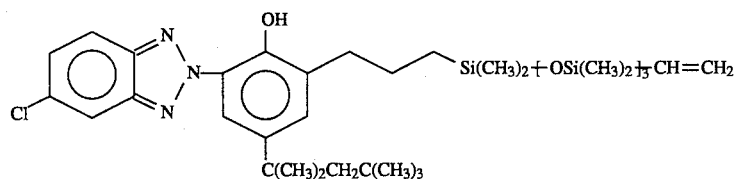

VIIIa

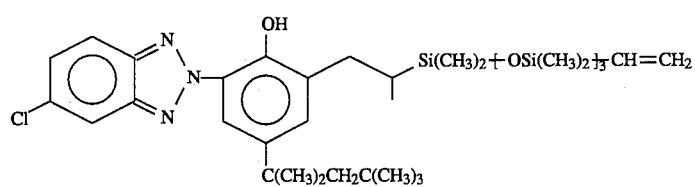

VIIIb

EXAMPLE 9

Example 1 is repeated except that I is replaced by:

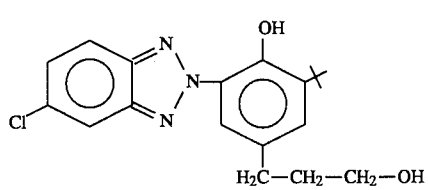

IX

A yellow, transparent liquid is obtained. $^1$H-NMR analysis shows the following compound to be present:

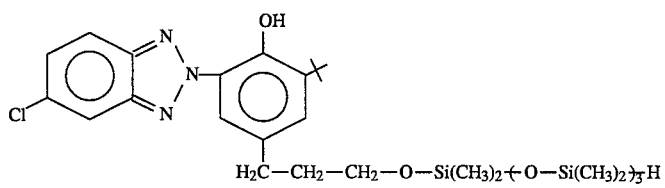

IXa

EXAMPLE 10

Example 2 is repeated except that II is replaced by IXa. A yellow transparent viscous livid is obtained. $^1$H-NMR analys is shows the following compound to be present:

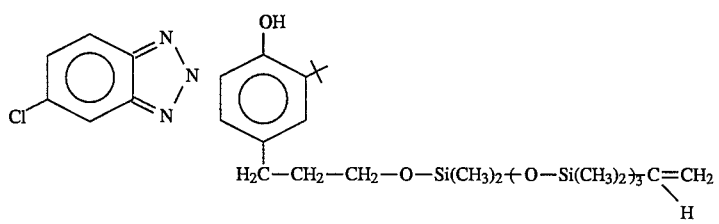

X

EXAMPLE 11

Example 10 is repeated except that the acetylene is replaced with 1,3-butadiene. A clear, yellow viscous liquid is obtained. $^1$H-NMR analysis shows the following three compounds to be present:

(about 50%)

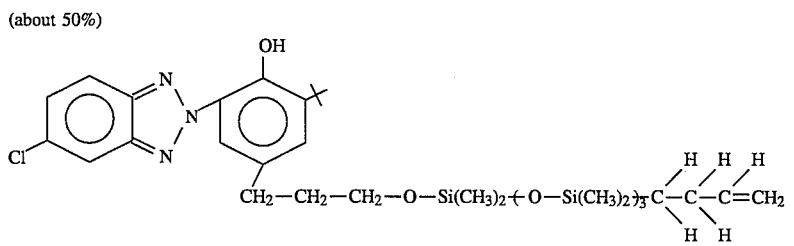

XIa (about 30%)

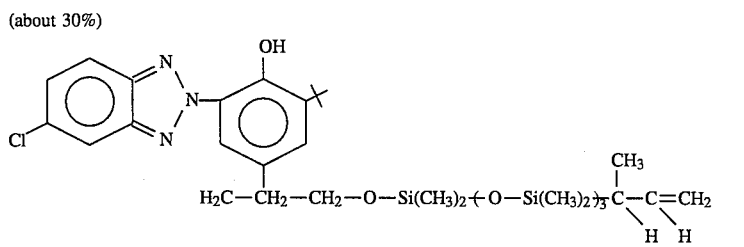

XIb (about 20%)

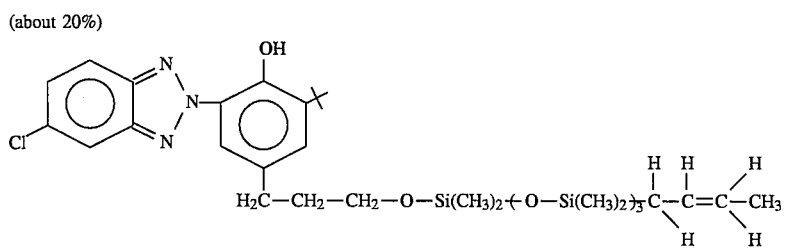

XIc

EXAMPLE 12

Example 1 is repeated except that the 1,1,3,3,5,5,7,7-octamethyl tetrasiloxane is replaced with the following cyclic tetrasiloxane:

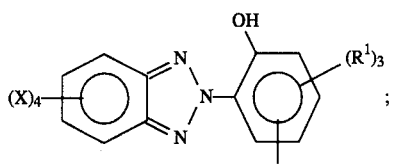

A yellow transparent liquid is obtained. High pressure liquid chromatography analysis shows two major components as follows to be present: XIIa (about 70%)

(about 70%)                                                    XIIa

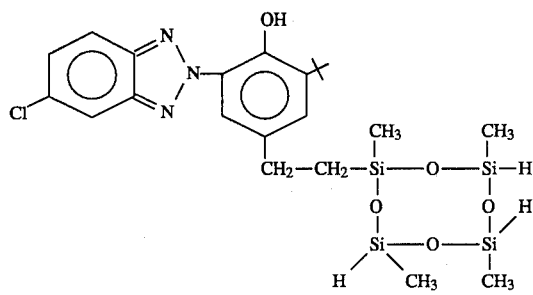

(about 30%)                                                    XIIb

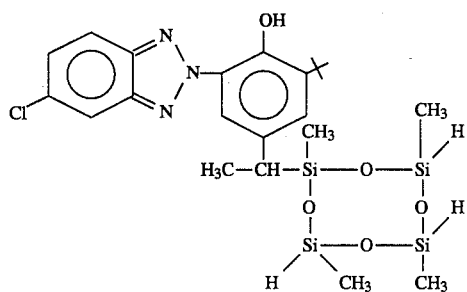

EXAMPLE 13

Example 2 is repeated except that II is replaced by the XIIa/XIIb mixture. A yellow viscous liquid is obtained and is found, by $^1$H-NMR analysis, to include the following compounds:

(about 70%)                                                    XIIIa

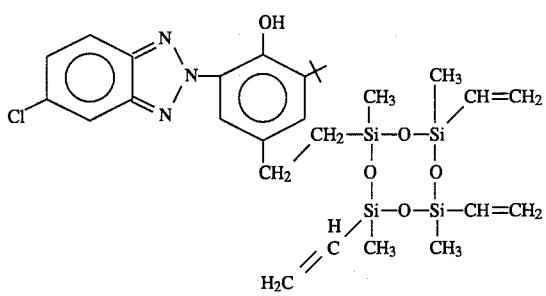

(about 30%)                                                    XIIIb

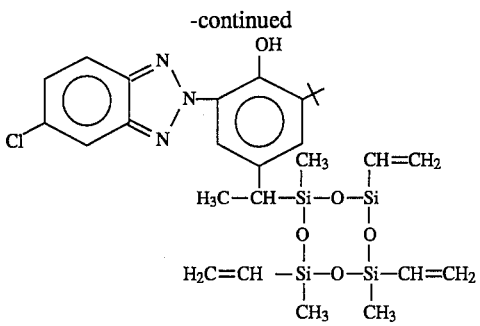

EXAMPLE 14

Example 1 is repeated except that I is replaced with 12 g of a compound having the following formula:

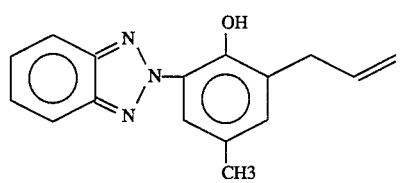
XIVa and the 1,1,3,3,5,5,7,7-octamethyltetrasiloxane is replaced with 4 g of polymethyl hydrosiloxane having the following formula:

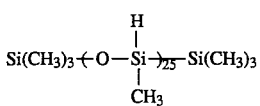
XIVb

A transparent yellow viscous liquid is obtained. The product is identified by $^1$H-NMR to have the following formula:

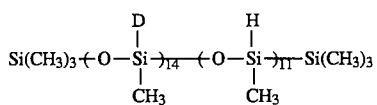
XIVc where D is XIVa.

EXAMPLE 15

Example 2 is repeated except that II is replaced by XIVc. A yellow viscous oil is obtained. The product is found to have the following structure by $^1$H-NMR analysis:

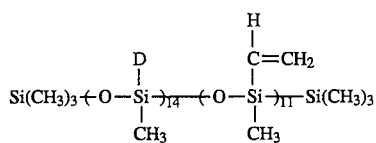
XV

EXAMPLES 16–24

Example 3 is repeated eight (8) times. In each repetition, III is replaced with a different one of the final products obtained in Examples 7 to 15. The UV cutoff of each of the slabs is obtained.

These UV cutoff results indicate that each of these slabs has very good UV light absorbing properties.

While this invention has been described with respect to various specific examples and embodiments, it is to be understood that the invention is not limited thereto and that it can be variously practiced within the scope of the following claims.

What is claimed:

1. A compound having one of the following formulas

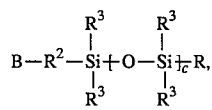

(1)

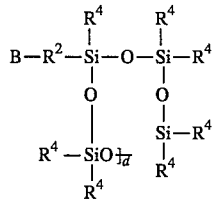

(2)

and mixtures thereof, wherein B is

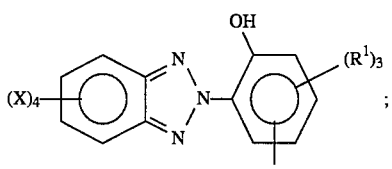

each x is independently selected from the group consisting of H, monovalent hydrocarbon radicals, monovalent substituted hydrocarbon radicals, hydroxyl radicals, amino radicals, carboxyl radicals, alkoxy radicals, substituted alkoxy radicals, and halogen radicals; each $R^1$ is independently selected from the group consisting of H, alkyl radicals, alkoxy radical, hydroxyl radicals, amino radicals and carboxyl radicals; $R^2$ is selected from the group consisting of divalent hydrocarbon radicals, divalent substituted hydrocarbon radicals, oxo, divalent oxyhydrocarbon radicals and divalent substituted oxyhydrocarbon radicals; each $R^3$ is independently selected from the group consisting of alkyl radicals, substituted alkyl radicals, alkoxy radicals, substituted alkoxy radicals, H, alkenyl radicals, substituted alkenyl radicals, $R^2$-B, aryl radicals, substituted aryl radicals and fluoro radical; R is selected from the group consisting of H, alkenyl radicals and substituted alkenyl radicals, alkenoxy radicals, substituted alkenoxy radicals, acryloxy alkyl radicals and substituted acryloxy alkyl radicals; each $R^4$ is independently selected from the group consisting of R and $R^3$, provided that at least one of the $R^4$s is R; c is an integer in the range of 1 to about 10,000; and d is an integer in the range of 0 to about 100.

2. The compound of claim 1 wherein each $R^3$ is independently selected from the group consisting of alkyl radicals and aryl radicals, and said alkenyl radicals and substituted alkenyl radicals which contain a terminal carbon-carbon double bond have 2 to about 6 carbon atoms.

3. The compound of claim 1 selected from the group consisting of compounds having the structure (1) and the mixtures thereof, and $R^2$ is bonded to the ortho position or to the para position relative to the phenolic hydroxyl group of B.

4. The compound of claim 3 wherein $R^2$ is bonded to the ortho position relative to the phenolic hydroxyl group of B.

5. The compound of claim 4 wherein all of the $R^1$s are H.

6. The compound of claim 1 wherein no more than one of the Xs is other than H, no more than one of the $R^1$s is other than H, each $R^3$ is independently selected from the group consisting of alkyl radicals having 1 to about 4 carbon atoms, substituted alkyl radicals having 1 to about 4 carbon atoms, alkoxy radicals having 1 to about 4 carbon atoms, substituted alkoxy radicals having 1 to about 4 carbon atoms, phenyl radicals and substituted phenyl radicals.

7. The compound of claim 1 wherein each $R^3$ is a methyl radical and c is an integer in the range of 1 to about 4 and d is an integer in the range of 0 to about 3.

8. The compound of claim 1 wherein $R^2$ is an alkylene radical.

9. A compound having the formula

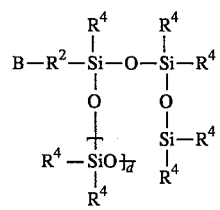

wherein B is

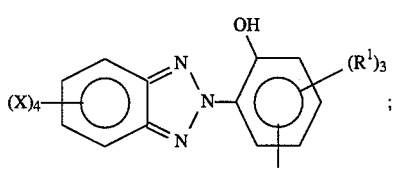

each x is independently selected from the group consisting of H, monovalent hydrocarbon radicals, monovalent substituted hydrocarbon radicals, hydroxyl radicals, amino radicals, carboxyl radicals, alkoxy radicals, substituted alkoxy radicals, and halogen radicals; each $R^1$ is independently selected from the group consisting of H, alkyl radicals, alkoxy radical, hydroxyl radicals, amino radicals and carboxyl radicals; $R^2$ is selected from the group consisting of divalent hydrocarbon radicals, divalent substituted hydrocarbon radicals, oxo, divalent oxyhydrocarbon radicals and divalent substituted oxyhydrocarbon radicals; each $R^4$ is independently selected from the group consisting of alkyl radicals, substituted alkyl radicals, alkoxy radicals, substituted alkoxy radicals, H, alkenyl radicals, substituted alkenyl radicals, $R^2$-B, aryl radicals, substituted aryl radicals, fluoro radical, alkenoxy radicals, substituted alkenoxy radicals, acryloxy alkyl -radicals and substituted acryloxy alkyl radicals, provided that at least one of the $R^4$s is selected from the group consisting of H, alkenyl radicals, substituted alkenyl radicals, alkenoxy radicals, substituted alkenoxy radicals, acryloxy alkyl radicals and substituted acryloxy alkyl radicals; and d is an integer in the range of 0 to about 100.

10. The compound of claim 9 wherein said alkenyl radicals and substituted alkenyl radicals which contain a terminal carbon-carbon double bond have 2 to about 6 carbon atoms.

11. The compound of claim 9 wherein no more than one of the Xs is other than H, and no more than one of the $R^1$s is other than H.

12. The compound of claim 9 wherein d is an integer in the range of 0 to about 3.

13. The compound of claim 9 wherein $R^2$ is an alkylene radical.

14. A method for producing an ultraviolet light absorbing compound comprising:

contacting a functional benzotriazole derivative with a siloxane component having at least two functional hydride groups at conditions effective to chemically react the functional group of the benzotriazole derivative with one of the hydride groups of the siloxane component, thereby forming a hydride functional benzotriazole derivative.

15. The method of claim 14 which further comprises contacting said hydride functional benzotriazole derivative with a functional component selected from the group consisting of compounds containing a plurality of carbon-carbon multiple bonds, compounds containing a carbon-carbon triple bond, compounds with both a hydroxyl group and a carbon-carbon multiple bond, compounds with an acryloxy alkyl group and a carbon-carbon multiple bond and mixtures thereof at conditions effective to chemically react the hydride group of said hydride functional benzotriazole derivative with a functional group present in said functional component, thereby forming an unsaturation functional benzotriazole derivative.

16. The method of claim 14 wherein said contacting occurs in the presence of a platinum group metal-containing catalyst in an amount effective to promote said chemical reaction.

17. The method of claim 15 wherein each of said contactings occurs in the presence of an effective amount of platinum group metal-containing catalyst.

* * * * *